United States Patent [19]

Buchbinder et al.

[11] Patent Number: 5,267,958
[45] Date of Patent: Dec. 7, 1993

[54] EXCHANGE CATHETER HAVING EXTERIOR GUIDE WIRE LOOPS

[75] Inventors: Maurice Buchbinder, San Diego; Glen Lieber, Poway; Ronald J. Solar, San Diego; Leo R. Roucher, Jr., Escondido, all of Calif.

[73] Assignee: Medtronic, Inc., Minneapolis, Minn.

[21] Appl. No.: 859,769

[22] Filed: Mar. 30, 1992

[51] Int. Cl.⁵ .................................. A61M 29/00
[52] U.S. Cl. .......................... 604/96; 604/280; 606/194
[58] Field of Search ............... 128/656-658, 128/772; 606/192, 194; 604/49, 52, 96, 101-102, 280

[56] References Cited

U.S. PATENT DOCUMENTS

| | | | |
|---|---|---|---|
| 4,471,766 | 9/1984 | Terayama | 128/6 |
| 4,581,017 | 4/1986 | Sahota | 604/101 |
| 4,748,982 | 6/1988 | Horzewski | 128/344 |
| 4,762,129 | 8/1988 | Bonzel | 128/344 |
| 4,771,782 | 9/1988 | Millar | 128/637 |
| 4,824,435 | 4/1989 | Giesy | 604/49 |
| 4,850,358 | 7/1989 | Millar | 128/637 |
| 4,988,356 | 1/1991 | Crittenden | 606/192 |
| 5,040,548 | 8/1991 | Yock | 128/898 |
| 5,046,497 | 9/1991 | Millar | 128/637 |
| 5,057,120 | 10/1991 | Farcot | 606/194 |
| 5,061,273 | 10/1991 | Yock | 606/194 |
| 5,180,367 | 1/1993 | Kontos et al. | 604/101 |

FOREIGN PATENT DOCUMENTS 0380227  1/1990  European Pat. Off. .

*Primary Examiner*—C. Fred Rosenbaum
*Assistant Examiner*—Corrine Maglione
*Attorney, Agent, or Firm*—Dianne M. F. Plunkett; Harold R. Patton

[57] ABSTRACT

A balloon catheter is disclosed having a catheter body and one or more loops external to the body and spaced from the balloon for insertion of a guidewire. A peelable sheath with a guidewiare lumen can instead be mounted exterior to the catheter body for holding the guidewire. The catheter body may optionally be reinforced with a stylet.

12 Claims, 1 Drawing Sheet

EXCHANGE CATHETER HAVING EXTERIOR GUIDE WIRE LOOPS

FIELD OF THE INVENTION

This invention relates to catheters which are exchangeable over a guidewire.

BACKGROUND OF THE INVENTION

In some catheterization therapies, a first catheter is preferably removed from the body after therapy and replaced with a second catheter.

One example of this exchange is in the use of balloon catheters in the treatment of stenosis in arteries. A current technique is the expansion of a partially occluded lumen in an artery through the use of a first balloon of a low profile. Once a lesion is opened, a larger balloon may be used to complete the opening of the occluded area.

The exchange of catheters can be a complex task. Prior art catheters commonly were inserted over a guidewire which extended in a lumen through the catheter. It was difficult to feed such a catheter onto a guidewire while a guidewire was in the body because of friction encountered when feeding the catheter through the artery. Additionally, the guidewire must be held while a catheter is loaded over it. Previously a physician loaded the catheter over a guidewire extension outside of the body and then slid it over the portion of the guidewire inside the body. This required a long guidewire extension outside the body as the guidewire extension had to be longer than the catheter. This long guidewire extension was difficult to keep out of the way during the surgical process. It also required an additional individual to handle the guidewire during the exchange process.

Various techniques have been tried to overcome this. For example, the catheter disclosed in U.S. Pat. No. 4,762,129 to Bonzel has a short lumen through the interior of a balloon. In Bonzel, the balloon lumen rides on the guidewire and the guidewire is outside the rest of the catheter body. In this way, only a portion of the guidewire which is as long as the balloon need extend outside the body for loading. The catheter itself must be stiff enough to be independently pushed through the artery.

Rapid exchange catheter art includes internal dual lumen apparatus and related devices such as U.S. Pat. Nos. 5,061,273 and 5,040,548 to Yock. Other rapid exchange techniques include slitted exchange sleeves such as that shown in U.S. Pat. No. 4,748,982 to Horzewski or U.S. Pat. No. 4,824,435 to Giesy as well as guiding tip rings such as U.S. Pat. No. 4,824,435 to Giesy. The narrow loop width of such guiding tip rings offer little support and reduce the pushability and tracking of their attached devices.

This description of art is not intended to constitute an admission that any patent, publication or other information referred to is "prior art" with respect to this invention, unless specifically designated as such. In addition, this section should not be construed to mean that a search has been made or that no other pertinent information as defined in 37 C.F.R. § 1.56(a) exists.

What is needed is a catheter design with a low profile through the balloon area, preferably with support for a guidewire in more locations along the catheter, to aid in pushability as well as aiding the tracking of the attached device. Additionally, a catheter with a smaller shaft size is desirable. Current fixed wire catheters, sometimes known as balloons on wires, are unable to maintain position within a select vessel as easily as over-the-wire catheters. A catheter is needed which allows a wire to be left behind following therapy. The wire is then advanced with the catheter across the diseased area. The wire is deployed distal to the diseased area and the catheter is removed.

SUMMARY OF THE INVENTION

The present invention relates to a catheter which has means, mounted external to a catheter body and spaced apart from the therapy means or balloon, for insertion of a guidewire. The external means is preferably one or more loops mounted on one side of the catheter body. The external loops can all be mounted proximally to the balloon or one external loop can be mounted distally to the balloon and the balance of the external loops mounted proximally to the balloon.

In another embodiment, the invention includes a peelable sheath mounted on the exterior of a catheter body including a lumen for holding the guidewire. The external loops may also be peelable.

In another embodiment, the catheter body is reinforced with a stylet.

DETAILED DESCRIPTION OF THE PREFERRED EMBODIMENTS

A first embodiment of the present invention, as illustrated in

Figure 1:
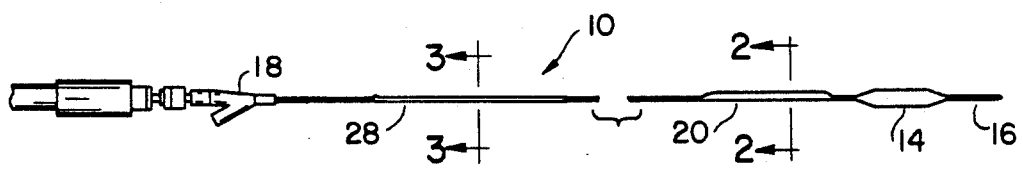
FIG. 1 is a side plan view of a catheter embodying the present invention.

FIG. 1, is a catheter 10 which includes a body 12, a therapy means such as balloon 14, distal tip 16, and control means 18. For the practice of the present invention, many types of catheters known in the prior art may be used. The control means 18, balloon 14 and distal tip 16 may be of various designs and sizes know by those skilled in the art.

Figure 2:
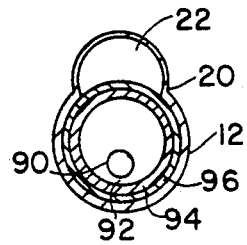
FIG. 2 is a cross-sectional view taken on line 2—2 of FIG. 1.
Figure 4:
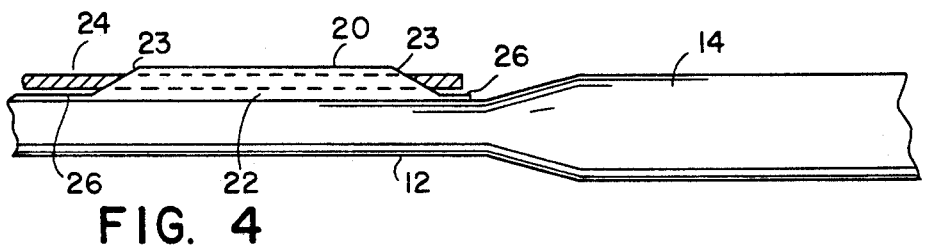
FIG. 4 is an enlarged partially broken away view of the guidewire lumen of the catheter of FIG. 1, with a loop in cross-section.

Mounted on body 12, spaced apart proximally from balloon 14, is a wire guiding means 20. In the embodiment shown, it is a guidewire loop or keeper 20 which is mounted on catheter body 12 so as to form a guidewire path or lumen 22 as illustrated in the cross-sectional view of FIG. 2. The catheter body 12 consists of a spring coil 94 with a jacket 96, of polyethylene, for example. Keeper 20, in this embodiment, is a partial cylinder of metallic or polymer material (PE, PVC, or similar known materials) approximately 25 cm long. Keeper 20 is affixed such as with glue as, for example, with cyanoacrylate, to catheter body 12, as at location 26. Insertion of a guidewire 24 through path 22 is illustrated in FIG. 4. Guidewire 24 rides in keeper 20 just as a belt fits in a belt loop or buckle keeper. The guidewire 24 will be more pushable and track better as the length of keeper 20 increases.

In FIG. 4, keeper 20 may be formed of the material of balloon 14. A skive 23 is cut to open both ends of keeper 20. Also mounted on catheter body 12 is sheath 28. Sheath 28 is preferably a cylinder mounted on catheter body 12 with a weakened slit 30 for removal by peeling, i.e., a "peelable sheath". The guidewire 24 will be more pushable and track better as the length of keeper 20 increases.

Figure 3:
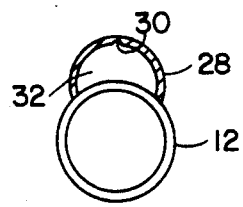
FIG. 3 is a cross-sectional view taken on line 3—3 of FIG. 1.

In the preferred embodiment, sheath 28 of FIG. 3 is formed of a polymer such as PET, polyethylene or polyethylene copolymers. In operation, one method of using catheter 10 is to insert the entire catheter with guidewire 24 loaded through a lumen 32 of sheath 28 and through lumen 22 of keeper 20. If an exchange is needed, catheter 10 is withdrawn proximally along guidewire 24. As sheath 28 is exposed outside of the body, sheath 28 is split and peeled away so that guidewire 24 is freed from its connection at that point with catheter body 12. Catheter body 12 slides along guidewire 24 by means of keeper 20. When catheter 10 is outside the body, it is removed from guidewire 24. A successive catheter with a keeper 20 is inserted over guidewire 24 and inserted into the body for the successive therapy.

Various combinations of sheath 28 and keeper 20 may be used by those skilled in the art. Suggested embodiments appear in the other figures.

Figure 5:
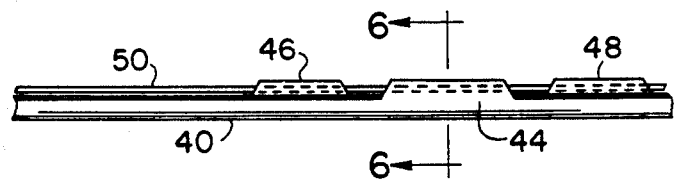
FIG. 5 is a side plan view partially broken away of an alternative embodiment of the present invention.

FIG. 5 illustrates a catheter 40 with a body 42 and a balloon 44.

Figure 6:
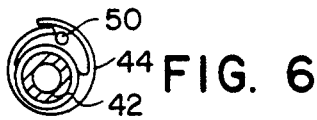
FIG. 6 is an enlarged cross-sectional view taken on line 6—6 of FIG. 5.

First keeper 46 is mounted on catheter body 42 proximal to balloon 44. Second keeper 48 is mounted distally to balloon 44 and catheter body 42. A guidewire 50 is illustrated inserted through first keeper 46 and second keeper 48. In this embodiment, guidewire 50 extends past uninflated balloon 44. For insertion, balloon 44 is wrapped around guidewire 50. An example of a technique for wrapping balloon 44 is illustrated in FIG. 6. Those skilled in the art will recognize that there are other positions in which balloon 44 could be wrapped or folded. Once catheter 40 is in place, guidewire 50 may be withdrawn from second keeper 48 to a position proximal of balloon 44 before balloon 44 is inflated. Suitable lengths of first keeper 46 and second keeper 48 range from one to two cm. Those skilled in the art will recognize that guidewire 50 will be more pushable and track better as the length of the first keeper 46 and the second keeper 48 increase and as additional keepers beyond one keeper are added.

Figure 7:
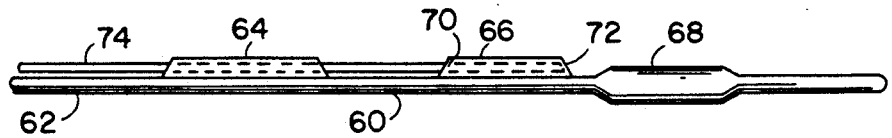
FIG. 7 is a side elevational view of an alternative embodiment of the present invention.

Another embodiment is illustrated in FIG. 7 where catheter 60 includes a catheter body 62 and first and second keepers 64 and 66, respectively, both of which are mounted proximal to balloon 68. In this embodiment, keeper 64 is constructed as previously disclosed. Keeper 66 has a central lumen 70 which is open to the proximal end of keeper 66 as discussed above. A distal end 72 of keeper 66, however, is closed. In this embodiment, guidewire 74 is mounted through keeper 64 and through keeper 66 up against end 72. In this way, guidewire 74 may be used to push catheter 60. Furthermore, guidewire 74 may be retracted or catheter 60 advanced until distal end of guidewire 74 rests in the space between keeper 64 and keeper 66. Guidewire 74 can then be advanced such that it rests external to keeper 66. Catheter 60 is now connected to guidewire 74 via keeper 64. Since guidewire 74 is no longer within the occluded keeper 66, catheter 60 can be withdrawn leaving guidewire 74 in place within the vessel thereby permitting easy exchange of catheters. Suitable lengths of keeper 64 and keeper 66 range from one to two cm. Those skilled in the art will recognize that guidewire 74 will be more pushable and track better as the length of keeper 64 and keeper 68 increase and as additional keepers beyond one keeper are added.

Figure 8:
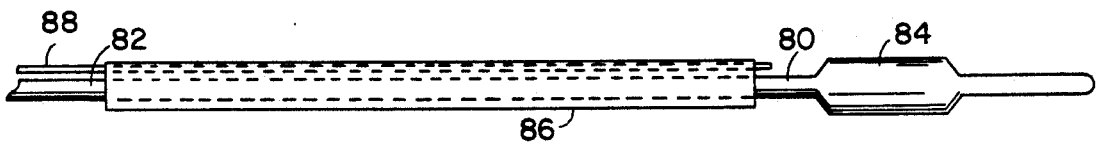
FIG. 8 is a side elevational view of an alternative embodiment of the present invention.

The alternative embodiment illustrated in FIG. 8 includes a catheter 80 with a body 82 and balloon 84. Mounted over catheter body 82, proximal to balloon 84 is a long sheath 86. Sheath 86 could be mounted utilizing a variety of techniques as, for example, adhesively, frictionally or thermally. Sheath 86 materials can include, for example, biocompatible materials such as polyethylene, nylon or Teflon ®. Sheath 86 is peelable as disclosed above. In this embodiment, guidewire 88 is mounted through sheath 86. When exchange is necessary, catheter 80 is withdrawn and sheath 86 is peeled away from guidewire 88 as catheter 80 exits the body. Keepers in other embodiments such as keeper 64 could be similarly peelable.

A catheter constructed according to the present invention can also improve pushability by optionally having a stylet 90 built into the catheter 10 for reinforcement so that the catheter 10 can be more easily pushed along the external guidewire 24. The stylet 90 is a rigid wire mounted to the length of the interior wall 92 of the spring coil 94. Mounting can be accomplished by welding, brazing or any other technique of affixing metal to metal. The stylet 90 could be implemented in any of the invention embodiments disclosed herein.

The preceding specific embodiments are illustrative of the practice of the invention. It is to be understood, however, that other expedients known to those skilled in the art or disclosed herein ma be employed without departing from the spirit of the invention or the scope of the appended claims.

What is claimed is:

1. A medical catheter comprising:
   an elongate body having a proximal end and a distal end;
   a therapy means mounted on the body generally adjacent to the distal end for providing medical treatment;
   a first wire guiding means, mounted external to the body, for mounting over a guidewire, the first wire guiding means being a loop fixedly attached to the body and mounted proximal to the therapy means; and
   a second wire guiding means mounted external to the body for mounting over a guidewire, the second wire guiding means being a loop fixedly attached to the body and mounted distal to the therapy means.

2. A medical catheter comprising:
   an elongate body having a proximal end and a distal end;
   a therapy means mounted on the body generally adjacent to the distal end for providing medical treatment;
   a first wire guiding means, mounted external to the body for mounting over a guidewire, the first wire guiding means being a loop fixedly attached to the body and proximal to the therapy means, wherein the loop is a peelable sheath;

wherein the catheter is reinforced with a stiffening means mounted to the body; and wherein the stiffening means is a stylet.

3. A medical catheter comprising:

an elongate body having a proximal end and a distal end;

a therapy means mounted on the body generally adjacent to the distal end for providing medical treatment;

a first wire guiding means, mounted external to the body, for mounting over a guidewire, the first wire guiding means being a loop with an occluded distal end fixedly attached to the body and mounted proximal to the therapy means;

a second wire guiding means being a peelable sheath and mounted proximal to the first wire guiding means.

4. A method of inserting a catheter on a guidewire comprising:

providing a catheter with an angioplasty balloon having a first guidewire loop proximal to the balloon and a second guidewire loop distal to the balloon;

inserting a guidewire through the first loop and the second loop;

wrapping the balloon around the guidewire; and inserting the catheter and guidewire in the human body.

5. The method of claim 4, further comprising:

withdrawing the guidewire in the proximal direction so that the guidewire is proximal to the balloon; and inflating the balloon.

6. The method of claim 5, further comprising:

deflating the balloon; and withdrawing the catheter over the guidewire.

7. The method of claim 6 further comprising;

positioning the guidewire over the stenosis, inserting a different catheter with an angioplasty balloon over the guidewire into the body, inflating the balloon, deflating the balloon, withdrawing the catheter over the guidewire.

8. A method of inserting a catheter on a guidewire comprising:

providing a catheter with an angioplasty balloon having a first guidewire loop proximal to the balloon and a second guidewire loop proximal to the first guidewire loop;

inserting the guidewire through the first and second guidewire loops;

inserting the catheter and guidewire in a human body;

removing the guidewire from the first guidewire loop;

placing the guidewire external to the outside surface of the first guidewire loop; and allowing the catheter to be withdrawn over the second guidewire loop while maintaining access to a vessel being treated by keeping the guidewire in place in the vessel.

9. The method of claim 8 wherein the step of removing the guidewire from the first guidewire loop includes withdrawing the guidewire.

10. The method of claim 8 wherein the step of removing the guidewire from the first guidewire loop includes advancing the catheter.

11. The method of claim 8 wherein the distal end of the first guidewire loop is occluded.

12. The method of claim 11 further comprising;

positioning the guidwire over the stenosis, inserting a different catheter with an angioplasty balloon over the guidewire into the body, inflating the balloon, deflating the balloon, withdrawing the catheter over the guidewire.

* * * * *

UNITED STATES PATENT AND TRADEMARK OFFICE
CERTIFICATE OF CORRECTION

PATENT NO. : 5,267,958
DATED : Dec. 7, 1993
INVENTOR(S) : Dr. Maurice Buchbinder, et al.

It is certified that error appears in the above-indentified patent and that said Letters Patent is hereby corrected as shown below:

Col. 4, line 39, delete "ma", add --may--.

Signed and Sealed this

Fifth Day of July, 1994

Attest:

BRUCE LEHMAN

Attesting Officer     Commissioner of Patents and Trademarks